United States Patent
Arata et al.

(10) Patent No.: US 10,813,655 B2
(45) Date of Patent: Oct. 27, 2020

(54) MANIPULATOR

(71) Applicant: Kyushu University, National University Corporation, Fukuoka-shi, Fukuoka (JP)

(72) Inventors: Jumpei Arata, Fukuoka (JP); Makoto Hashizume, Fukuoka (JP); Susumu Oguri, Fukuoka (JP)

(73) Assignee: Kyushu University, National University Corporation, Fukuoka-shi, Fukuoka (JP)

( * ) Notice: Subject to any disclaimer, the term of this patent is extended or adjusted under 35 U.S.C. 154(b) by 193 days.

(21) Appl. No.: 15/755,932

(22) PCT Filed: Sep. 30, 2016

(86) PCT No.: PCT/JP2016/079179
§ 371 (c)(1),
(2) Date: Feb. 27, 2018

(87) PCT Pub. No.: WO2017/057761
PCT Pub. Date: Apr. 6, 2017

(65) Prior Publication Data
US 2018/0333164 A1    Nov. 22, 2018

(30) Foreign Application Priority Data

Oct. 2, 2015 (JP) ................. 2015-197194

(51) Int. Cl.
*A61B 17/29* (2006.01)
*A61B 34/00* (2016.01)
(Continued)

(52) U.S. Cl.
CPC ........ *A61B 17/29* (2013.01); *A61B 17/00234* (2013.01); *A61B 17/30* (2013.01);
(Continued)

(58) Field of Classification Search
CPC ........... A61B 17/29; A61B 2017/2937; A61B 2034/305; A61B 17/30; A61B 34/70;
(Continued)

(56) References Cited

U.S. PATENT DOCUMENTS

| 4,527,331 A | * | 7/1985 | Lasner | ............... A61B 17/3201 30/135 |
| 4,706,668 A | | 11/1987 | Backer | |

(Continued)

FOREIGN PATENT DOCUMENTS

| JP | 4460890 B2 | 5/2010 |
| WO | 2005046500 A1 | 5/2005 |
| WO | 2010/117051 A1 | 10/2010 |

OTHER PUBLICATIONS

Communication dated Feb. 22, 2019, issued by the European Patent Office in counterpart European Application No. 16851930.4.
(Continued)

*Primary Examiner* — Katherine M Shi
(74) *Attorney, Agent, or Firm* — Sughrue Mion, PLLC

(57) ABSTRACT

A manipulator includes a flexible actuating body, that includes a rectangular horizontal plate spring, a curved vertical plate spring which stands upright having a plate surface perpendicular to a plate surface of the horizontal plate spring, of which a base end is connected to one end of the horizontal plate spring in a longitudinal direction, which protrudes to one side in a width direction of the horizontal plate spring, which extends along the longitudinal direction of the horizontal plate spring, and of which a tip end in the extending direction is a portion bent in a direction opposite to the protruding direction, a shaft body which is connected to a tip end of the bent portion, and is rotatably supported at a center perpendicular to the plate surface of the horizontal
(Continued)

plate spring, and an actuator protruding in a radius direction from an outer circumference of the shaft body.

8 Claims, 11 Drawing Sheets

(51) Int. Cl.

| | |
|---|---|
| *A61B 17/00* | (2006.01) |
| *A61B 17/30* | (2006.01) |
| *A61B 17/32* | (2006.01) |
| *A61B 17/3201* | (2006.01) |
| *A61B 17/34* | (2006.01) |
| *B25J 9/00* | (2006.01) |
| *F16H 21/54* | (2006.01) |
| *A61B 34/30* | (2016.01) |
| *F16H 25/22* | (2006.01) |

(52) U.S. Cl.
CPC .. *A61B 17/3201* (2013.01); *A61B 17/320016* (2013.01); *A61B 17/3415* (2013.01); *A61B 34/70* (2016.02); *B25J 9/0009* (2013.01); *F16H 21/54* (2013.01); *A61B 2017/00318* (2013.01); *A61B 2017/00327* (2013.01); *A61B 2017/00398* (2013.01); *A61B 2017/2903* (2013.01); *A61B 2017/2937* (2013.01); *A61B 2017/305* (2013.01); *A61B 2034/305* (2016.02); *F16H 25/2204* (2013.01)

(58) Field of Classification Search
CPC .... A61B 17/00234; A61B 2017/00318; A61B 2017/00327; A61B 2017/2926; A61B 2017/305; A61B 2017/00867; A61B 2017/2917; A61B 2017/2939; A61B 17/1285; A61B 17/1227; A61B 17/122; A61B 17/083
See application file for complete search history.

(56) References Cited

U.S. PATENT DOCUMENTS

| | | |
|---|---|---|
| 5,964,780 A | 10/1999 | Balazs |
| 2008/0039892 A1 | 2/2008 | Mitsuishi et al. |
| 2010/0160940 A1 | 6/2010 | Lutze et al. |
| 2011/0301637 A1 | 12/2011 | Kerr et al. |
| 2013/0046336 A1 | 2/2013 | Blumenkranz |

OTHER PUBLICATIONS

Gary S. Guthart et al., "The Intuitive™ Telesurgery System: Overview and Application", Proceedings of the 2000 IEEE International Conference on Robotics & Automation San Francisco, CA Apr. 2000, (4 Pages Total).

International Search Report, issued by International Searching Authority in corresponding International Application No. PCT/JP2016/079179, dated Nov. 22, 2016, (PCT/ISA/210).

Written Opinion, issued by International Searching Authority in corresponding International Application No. PCT/JP2016/079179, dated Nov. 22, 2016, (PCT/ISA/237).

Translation of Written Opinion, issued by International Searching Authority in corresponding International Application No. PCT/JP2016/079179, dated Nov. 22, 2016, (PCT/ISA/237).

* cited by examiner

FIG.7

DISPLACEMENT DIRECTION OF ACTUATOR BY
ONE PAIR OF HORIZONTAL PLATE SPRINGS

| | | HORIZONTAL PLATE SPRING OF FIRST FLEXIBLE ACTUATING BODY | |
|---|---|---|---|
| | | PUSH | PULL |
| HORIZONTAL PLATE SPRING OF SECOND FLEXIBLE ACTUATING BODY | PUSH | OPEN | $-Y$ |
| | PULL | Y | CLOSE |

FIG.8

DISPLACEMENT DIRECTION OF ACTUATOR BY ONE
PAIR OF OUTER HORIZONTAL PLATE SPRINGS

| | | HORIZONTAL PLATE SPRING OF FIRST FLEXIBLE ACTUATING BODY | |
|---|---|---|---|
| | | PUSH | PULL |
| HORIZONTAL PLATE SPRING OF SECOND FLEXIBLE ACTUATING BODY | PUSH | Z | $-X$ |
| | PULL | X | $-Z$ |

MANIPULATOR

TECHNICAL FIELD

The present invention relates to a manipulator.

BACKGROUND ART

In recent years, minimally invasive surgery represented, for example, by laparoscopic surgery attracts attention as one method of a surgical operation. In minimally invasive surgery, surgical instruments such as endoscopes or forceps are inserted into a body through a small incision hole of approximately 5 to 10 mm opened in a body surface, and surgery is performed inside the body. Therefore, compared to ordinary surgical operations (for example, open chest surgery or open abdominal surgery), there is an advantage that damage to the body of a patient at the time of surgery and pain after surgery can be minimized.

Since forceps used for minimally invasive surgery are restricted in postures thereof by incision holes in the body of the patient, the forceps can only approach from a limited direction to an affected area. In order to easily perform work, such as grasping and ligating, under such conditions, there is a demand for the development of bending forceps (that is, multi-degree-of-freedom manipulator) configured to bend the tip end part of the forceps in multiple directions.

As a product of this type of multi-degree-of-freedom manipulator, for example, "da Vinci surgical system" by Intuitive Surgical, Inc. is known (refer to Non Patent Literature 1). In the multi-degree-of-freedom manipulator of Non Patent Literature 1, a wire is employed as a tool for transmitting power from a driving device. By winding up the wire with the driving device, bending of a joint, opening and closing of a gripping portion, and the like are realized.

Patent Literature 1 is also cited as a related art regarding a multi-degree-of-freedom manipulator, for example. In the multi-degree-of-freedom manipulator disclosed in Patent Literature 1, a link mechanism is employed as a tool for transmitting power from a driving device.

CITATION LIST

Patent Literature

Patent Literature 1: Japanese Patent No. 4460890

Non Patent Literature

Non Patent Literature 1: Gary S. Guthart and J. Kenneth Salisbury, Jr., "The Intuitive (TM) Telesurgery System: Overview and Application", Proceedings of the 2000 IEEE International Conference on Robotics & Automation San Francisco, Calif. April 2000, pp. 618-621, 2000

SUMMARY OF INVENTION

Technical Problem

However, the wire driving that serves as the power transmission method employed in Non Patent Literature 1 has the following problems.

Firstly, since there is a concern that the wire may be "stretched" or "broken", the wire must be replaced frequently. For example, in the above-described "da Vinci surgical system", it is necessary to replace wires for approximately 10 surgeries. In addition, since the wire is wound around a plurality of gears or pulleys, it takes a lot of time and effort in detaching and mounting. Accordingly, an increase in running costs and maintenance load are caused.

Secondly, since the wire expands and contracts, there is a limit to the control accuracy of the joint or the gripping portion. In addition, there is also a disadvantage that the wire can transmit power only in one direction (drawing direction).

Thirdly there is a problem that it is difficult to sterilize and clean the wire. Therefore, in the multi-degree-of-freedom manipulator of the related art, preoperative and postoperative sterilization and cleaning work is extremely complicated.

In addition, the link mechanism that serves as the power transmission method employed in Patent Literature 1 has the following problems.

Firstly, in a case where a plurality of link mechanisms configured of a plurality of links are provided, the number of components increases, it is difficult to reduce the size and weight, and the product costs increase.

Secondly, when a rotation operation is performed by the plurality of link mechanisms, a bending radius (that is, swing radius) of a capturing device (for example, a first supporting body 16 of Patent Literature 1) becomes large, and it is difficult to smoothly move so as to approach the affected area at the time of surgery performed on the narrow site. This problem also occurs in wire driving that uses gears or pulleys.

The present invention has been made in consideration of the above-described circumstances of the related art, and an object of the present invention is to provide a manipulator in which wires that serve as a tool for transmitting power to a tip end portion that performs treatment with respect to an affected area can be eliminated, which can reduce the size, weight, and costs with a small number of components, and further which causes easy approach to the affected area.

Solution to Problem

In the present invention, there is provided a manipulator including: at least one flexible actuating body including a rectangular horizontal plate spring; a curved vertical plate spring which stands upright having a plate surface perpendicular to a plate surface of the horizontal plate spring, of which a base end is connected to one end of the horizontal plate spring in a longitudinal direction, which protrudes to one side in a plate width direction of the horizontal plate spring, which extends along the longitudinal direction of the horizontal plate spring, and of which a tip end in the extending direction is a bent portion bent in a direction opposite to the protruding direction; a shaft body which is connected to a tip end of the bent portion, is supported at a rotation center perpendicular to the plate surface of the horizontal plate spring, and becomes freely rotatable; and an actuator which is provided to protrude in a radius direction from an outer circumference of the shaft body.

According to the manipulator, the horizontal plate spring, the curved vertical plate spring, and the shaft body are disposed in series on the same plane to configure the flexible actuating body. The curved vertical plate spring is connected to the horizontal plate spring while the plate surface stands upright. When the other end in the longitudinal direction of the horizontal plate spring is pressed in the direction along the longitudinal direction, in a case where the shaft body is supported so as to be immovable within the same plane as described above, the flexible actuating body is deformed in a direction in which the curved vertical plate spring is further curved. Since the horizontal plate spring and the plate surface of the curved vertical plate spring are orthogonal to each other, the deformation direction of the curved vertical plate spring changes by 90°. In the curved vertical plate spring, most of the internal stress accumulated by the deformation is an elastic restoring force. A part of the elastic restoring force acts as a component force in a tangential direction of the outer circumference of the shaft body which generates a moment with respect to the shaft body.

In addition, in the present invention, there is provided the manipulator in which one side portion of a reinforcing portion having one pair of orthogonal side portions is fixed to the horizontal plate spring at a corner at which the horizontal plate spring and the curved vertical plate spring are connected to each other, and the other side portion of the reinforcing portion is fixed to the curved vertical plate spring at the corner.

According to the manipulator, a connecting portion between the horizontal plate spring and the curved vertical plate spring is reinforced by the reinforcing portion, and the rigidity is enhanced. Accordingly, due to the force transmitted from the horizontal plate spring, the curved vertical plate spring is less likely to twist. As a result, the transmission efficiency of the force transmitted from the horizontal plate spring to the curved vertical plate spring can increase.

In addition, in the present invention, there is provided the manipulator, including: one pair of the flexible actuating bodies, in which the pair of the flexible actuating bodies overlaps such that the protruding direction of a curve of the one flexible actuating body becomes opposite to the protruding direction of a curve of the curved vertical plate spring of the other flexible actuating body, is linked to each other to be freely rotatable at the rotation center by a common pin penetrating the shaft body of each of the pair of the flexible actuating bodies, and is accommodated on the inside of an outer tube from the other ends in the longitudinal direction of one pair of the horizontal plate springs to middle part in the longitudinal direction in one pair of the flexible actuating bodies.

According to the manipulator, since the protruding directions of the curved vertical plate springs of one pair of flexible actuating bodies are opposite to each other, the other ends in the longitudinal direction of each of the horizontal plate springs (that is, the side opposite to the actuator side) are pushed or pulled at the same time, and accordingly, each of the actuators can be moved close to and away from each other. In other words, when the actuator is a capturing device, such as forceps or tweezers in laparoscopic surgery, pinching becomes possible. In addition, in the manipulator, by pushing or pulling the other ends in the longitudinal direction of one pair of horizontal plate springs (that is, the side opposite to the actuator side) at the same time in the opposite directions, one pair of actuators can be rotated about the rotation center of the shaft body in the same direction. In other words, when the actuator is a capturing device, such as forceps or tweezers in laparoscopic surgery the capturing device can be rotated in forward and reverse directions while the capturing device is closed.

In addition, in the present invention, there is provided the manipulator in which the rotation center of the shaft body is disposed on an axis line that passes through a center in the plate width direction of the horizontal plate spring.

According to the manipulator, the rotation center of each of the shaft bodies is disposed to be shared and fixed by one pin on an extension line of the axis line of the horizontal plate spring. Accordingly, the manipulator can ensure the curved shape while suppressing the protrusion width between protrusion ends in the curved direction of one pair of curved vertical plate springs to be small.

In addition, in the present invention, there is provided the manipulator, further including: a holder which supports both ends of the pin, in which one ends of one pair of outer horizontal plate springs which sandwiches the horizontal plate springs of the pair of the flexible actuating bodies in parallel, and extends in the same direction as that of the horizontal plate spring, are connected to the holder, and the pair of outer horizontal plate springs is accommodated inside the outer tube from the other ends in the longitudinal direction to the middle parts in the longitudinal direction.

According to the manipulator, one pair of outer horizontal plate springs is disposed on the outside of one pair of horizontal plate springs sandwiching the horizontal plate springs. In other words, in the outer tube, one pair of horizontal plate springs and one pair of outer horizontal plate springs are disposed in four layers. The one pair of horizontal plate springs and the one pair of outer horizontal plate springs are independently pushed and pulled. One end in the longitudinal direction (that is, actuator side) of one pair of outer horizontal plate springs is fixed to the holder. The outer tube and the holder are disposed to be separated from each other with a gap having a predetermined width. Therefore, between the outer tube and the holder, only one pair of horizontal plate springs and one pair of outer horizontal plate springs sandwiching the horizontal plate springs which overlap in four layers are exposed. In the manipulator, when one pair of outer horizontal plate springs are pushed and pulled in reverse direction, one pair of outer horizontal plate springs is deformed (bent) in a direction of being inclined to one outer horizontal plate spring side together or in a direction of being inclined to the other outer horizontal plate spring together. The holder is displaced (tilted) due to the curve of the one pair of outer horizontal plate springs. At this time, one pair of horizontal plate springs disposed between one pair of outer horizontal plate springs is also passively bent in the same direction.

In addition, in the present invention, there is provided the manipulator in which one pair of guides which is in contact with curved outer surfaces of the curved vertical plate springs of each of the pair of the flexible actuating bodies is provided in the holder.

According to the manipulator, the deformation of the curved vertical plate spring in the direction of being further curved is restricted by the guide which is in contact with the curved outer surface. Accordingly, the deformation of the curved vertical plate spring in the bending direction due to the reaction force from the shaft body is restricted. As a result, it is possible to apply a large moment to the shaft body.

In addition, in the present invention, there is provided the manipulator in which one pair of spacers which is in contact with each of one pair of side end surfaces is provided on an inner surface of the outer tube along the longitudinal direction of the horizontal plate spring of each of the pair of the flexible actuating bodies.

According to the manipulator, a force for pushing and pulling the horizontal plate spring is converted into a moment for rotating the shaft body and transmitted. At this time, the flexible actuating body receives a force that moves the horizontal plate spring in the plate width direction by the reaction force from the shaft body. In the flexible actuating body, the movement of the horizontal plate spring in the plate width direction is regulated by the spacer. As a result, it is possible to increase the transmission efficiency of the force from the horizontal plate spring to the curved vertical plate spring, and to apply a large moment to the shaft body.

Advantageous Effects of Invention

According to the present invention, it is possible to eliminate wires, to reduce the size, weight, and costs with a small number of components, and to easily approach an affected area.

BRIEF DESCRIPTION OF DRAWINGS

FIG. 7 describes an operation illustrating the displacement direction of the actuator by one pair of horizontal plate springs.

FIG. 8 describes an operation illustrating the displacement direction of the actuator by one pair of outer horizontal plate springs.

DESCRIPTION OF EMBODIMENTS

Hereinafter, an embodiment in which a manipulator according to the present invention (hereinafter referred to as the embodiment) specifically disclosed will be described in detail with reference to the drawings as appropriate. However, detailed description more than necessary may be omitted in some cases. For example, detailed description of already well-known matters and redundant description on substantially the same configuration may be omitted in some cases. This is to avoid the unnecessary redundancy of the following description and to make it easy to understand for those skilled in the art. In addition, the attached drawings and the following description are provided to enable those skilled in the art to fully understand the present disclosure, and are not intended to limit the subject matter described in the claims. In addition, in the following embodiment, the manipulator according to the present invention will be described by exemplifying a manipulator used for laparoscopic surgery in a minimally invasive surgical procedure, for example.

Figure 1:
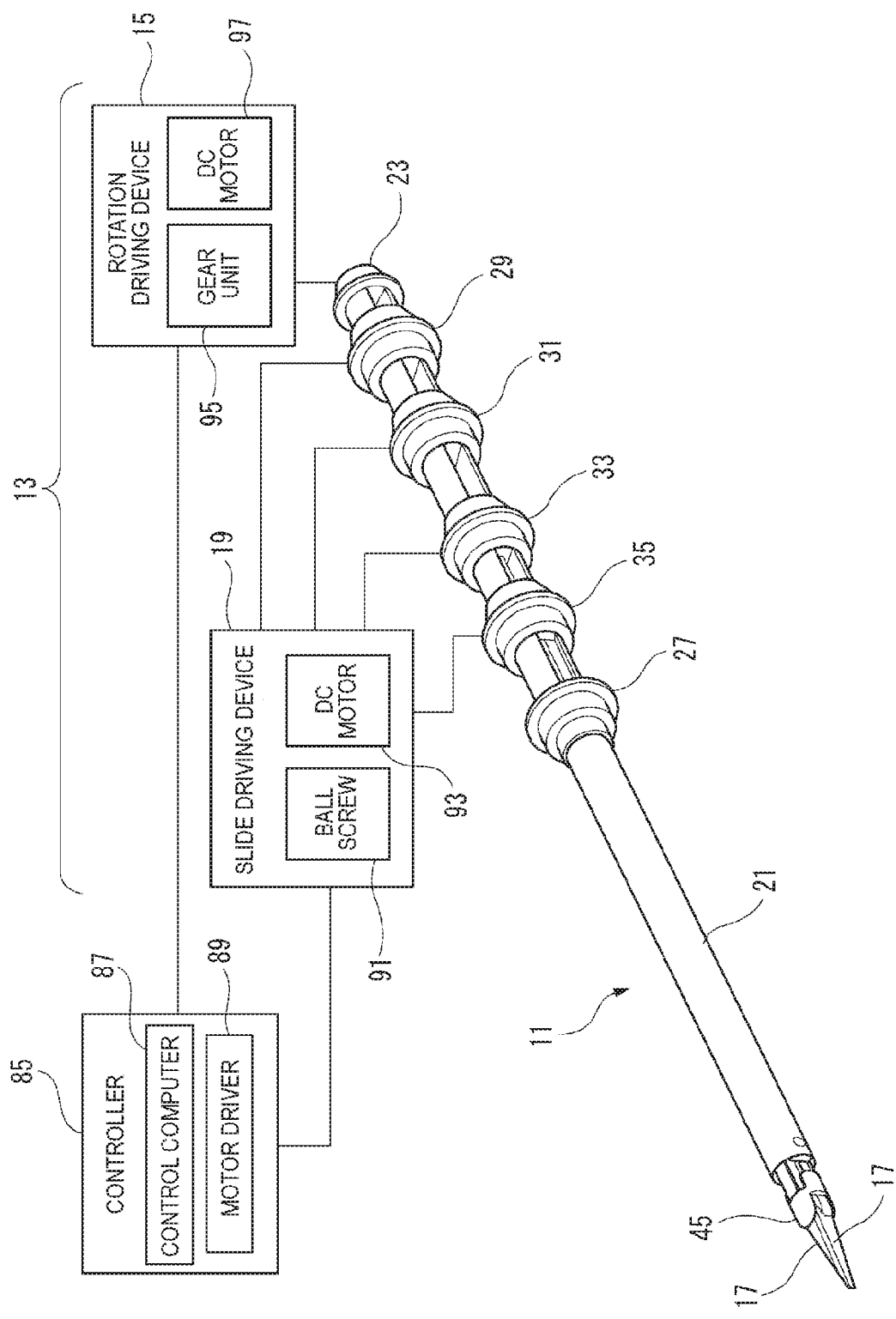
FIG. 1 is an external perspective view of a manipulator of an embodiment.

FIG. 1 is an external perspective view of a manipulator 11 of the embodiment.

The manipulator 11 of the embodiment is attached to a manipulator driving unit 13. The manipulator driving unit 13 is fixed to a link unit (not illustrated). In the manipulator 11, a tip end side is inserted into a trocar (not illustrated) fixed to the link unit. Together with the trocar, the manipulator 11 moves with multiple degrees of freedom around one rotation center by a link unit driven by a link driving unit (not illustrated).

The manipulator 11 rotates on the inside of the trocar by a rotation driving device 15 provided in the manipulator driving unit 13. In addition, an actuator 17 provided on the tip end side of the manipulator 11 is operated with multiple degrees of freedom by a slide driving device 19 provided in the manipulator driving unit 13. At least one actuator 17 configures an end effector. The end effector means an actual working part of a surgical instrument and includes, for example, a clamp, a capturing device, a scissors, a stapler, and a needle holder. One pair of actuators 17 can be used as end effectors, such as clamps, capturing devices, scissors, and staplers. One actuator 17 can be used as an end effector, such as a needle holder. In the embodiment, the end effector can also be used as a capturing device that can be configured with one actuator 17, but for the sake of more specific description, a capturing device configured with one pair of actuators 17 will be exemplified in the description.

In standard laparoscopic surgery, for example, the manipulator 11 is inserted through the above-described trocar that has passed through a small (approximately ½ inch) incision in the abdomen. A surgeon manipulates the end effector disposed at the internal surgical site via the manipulator 11 from the outside of the abdomen. The surgeon observes the procedure with a monitor (not illustrated) that displays an image of the surgical site taken from the laparoscope by the endoscope (not illustrated). A similar endoscopic procedure can be employed to arthroscopy, peritoneal lumenoscope, pelviscopy, renal pelvis, cystoscope, cisternoscopy, sinoscopy, hysteroscope, or urethral mirror.

The manipulator 11 includes an outer tube 21. The outer tube 21 is configured of, for example, a stainless steel tube, and is formed with an outer diameter of 6 mm. The outer tube 21 is formed with an outer diameter smaller than 8.5 mm of outer diameter of the outer tube in the above-described system of "da Vinci surgical system". The manipulator 11 is formed such that the distance from the tip end of the actuator 17 to the manipulator driving unit 13 is 125 to 300 mm. The outer circumference of the outer tube 21 is further covered with a sheath.

An end cap 23 is fixed to the base end side of the outer tube 21 in an insertion direction (that is, the side opposite to the actuator 17 side). The manipulator 11 integrally rotates in an e direction in FIG. 2 as the end cap 23 rotates by the rotation driving device 15 provided in the manipulator driving unit 13. A stopper 27 is fixed to the front side in the insertion direction of the end cap 23 (that is, on the actuator 17 side). The stopper 27 engages with the manipulator driving unit 13 to regulate the movement of the manipulator 11 in a longitudinal direction. Between the end cap 23 and the stopper 27, four sliders of a first outer slider 29, a first slider 31, a second slider 33, and a second outer slider 35 from the base end side (that is, the side opposite to the actuator 17 side), are respectively provided to be freely movable in the longitudinal direction of the outer tube 21. The four sliders (that is, the first outer slider 29, the first slider 31, the second slider 33, and the second outer slider 35) are inserted into the outer tube 21, and are respectively linked to the first outer slider shaft 37, the first slider shaft 39, the second slider shaft 41, and the second outer slider shaft 43 (refer to FIG. 3) which are elongated toward the tip end (that is, the actuator 17 side).

As a ball screw of the slide driving device 19 moves, each of the first outer slider shaft 37, the first slider shaft 39, the second slider shaft 41, and the second outer slider shaft 43 is moved (that is, pushed and pulled) in the longitudinal direction being independent from each other by the movement of the first outer slider 29, the first slider 31, the second slider 33, and the second outer slider 35. The end effector provided at the tip end of the outer tube 21 (that is, the actuator 17 side) operates with multiple degrees of freedom by the four shafts.

Figure 2:
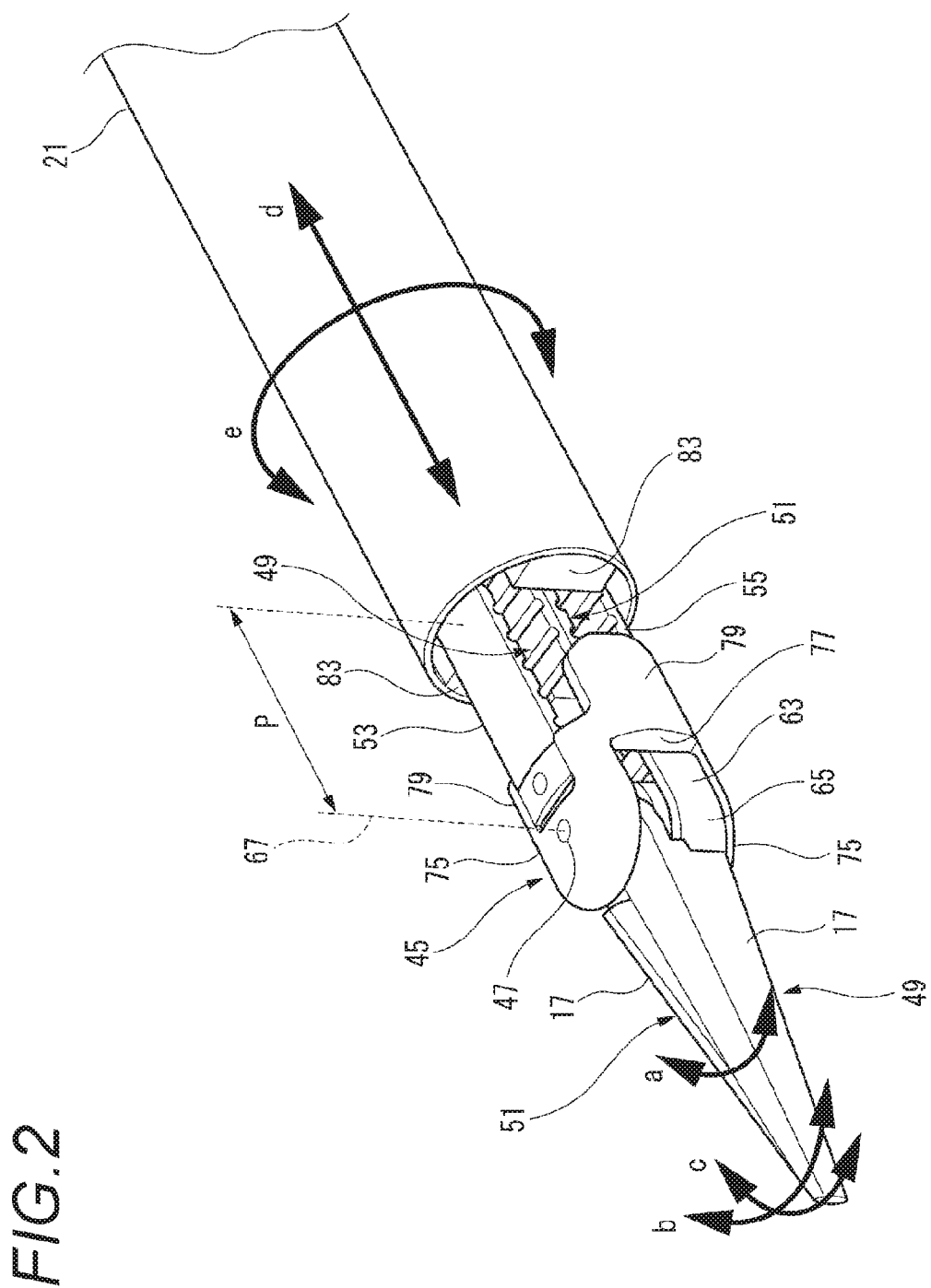
FIG. 2 is an enlarged perspective view of a main part of a tip end portion of the manipulator illustrated in FIG. 1.

FIG. 2 is an enlarged perspective view of a main part of a tip end portion of the manipulator 11 illustrated in FIG. 1.

The tip end portion of the manipulator 11 is configured with one pair of flexible actuating bodies, one pair of outer horizontal plate springs, a holder 45, and a pin 47. In the embodiment, one pair of flexible actuating bodies includes a first flexible actuating body 49 and a second flexible actuating body 51. In addition, one pair of outer horizontal plate springs also includes a first outer horizontal plate spring 53 and a second outer horizontal plate spring 55. The first outer horizontal plate spring 53, the first flexible actuating body 49, the second flexible actuating body 51, and the second outer horizontal plate spring 55 are formed so as to be elongated along the longitudinal direction with respect to the outer tube 21, and one end in the longitudinal direction extends from the inside of the outer tube 21. In the present specification, the direction on one end side is a direction on the tip end side (that is, the actuator 17 side) of the manipulator 11. The first outer horizontal plate spring 53, the first flexible actuating body 49, the second flexible actuating body 51, and the second outer horizontal plate spring 55 are accommodated in the outer tube 21 from the other ends in the longitudinal direction to the middle parts in the longitudinal direction.

Figure 3:
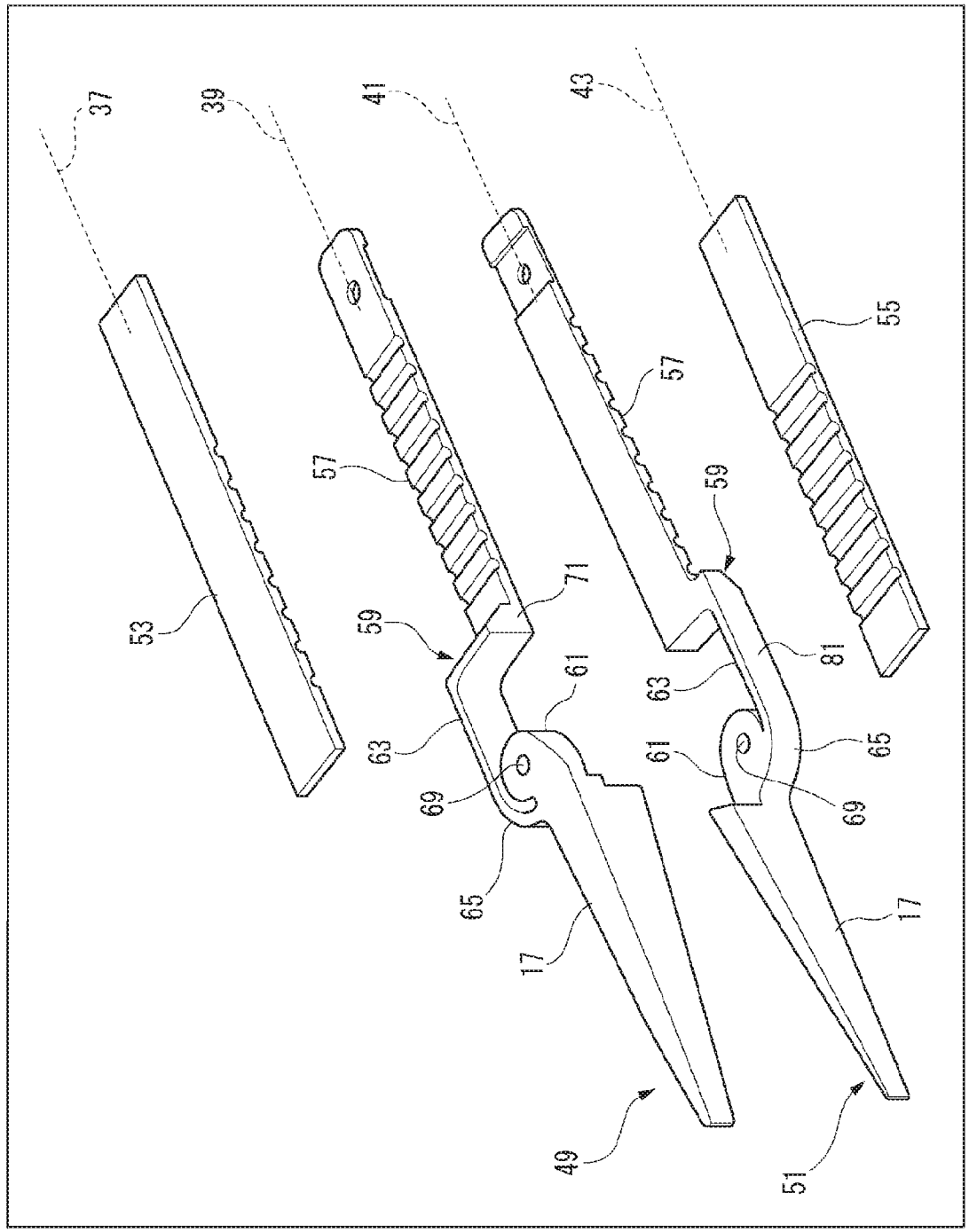
FIG. 3 is an exploded perspective view of a flexible actuating body and an outer horizontal plate spring which are illustrated in FIG. 2.

FIG. 3 is an exploded perspective view of the flexible actuating body and the outer horizontal plate spring which are illustrated in FIG. 2.

On the inside of the outer tube 21, the first outer horizontal plate spring 53 is connected to the first outer slider shaft 37. The first flexible actuating body 49 is connected to the first slider shaft 39. The second flexible actuating body 51 is connected to the second slider shaft 41. The second outer horizontal plate spring 55 is connected to the second outer slider shaft 43.

Figure 4:
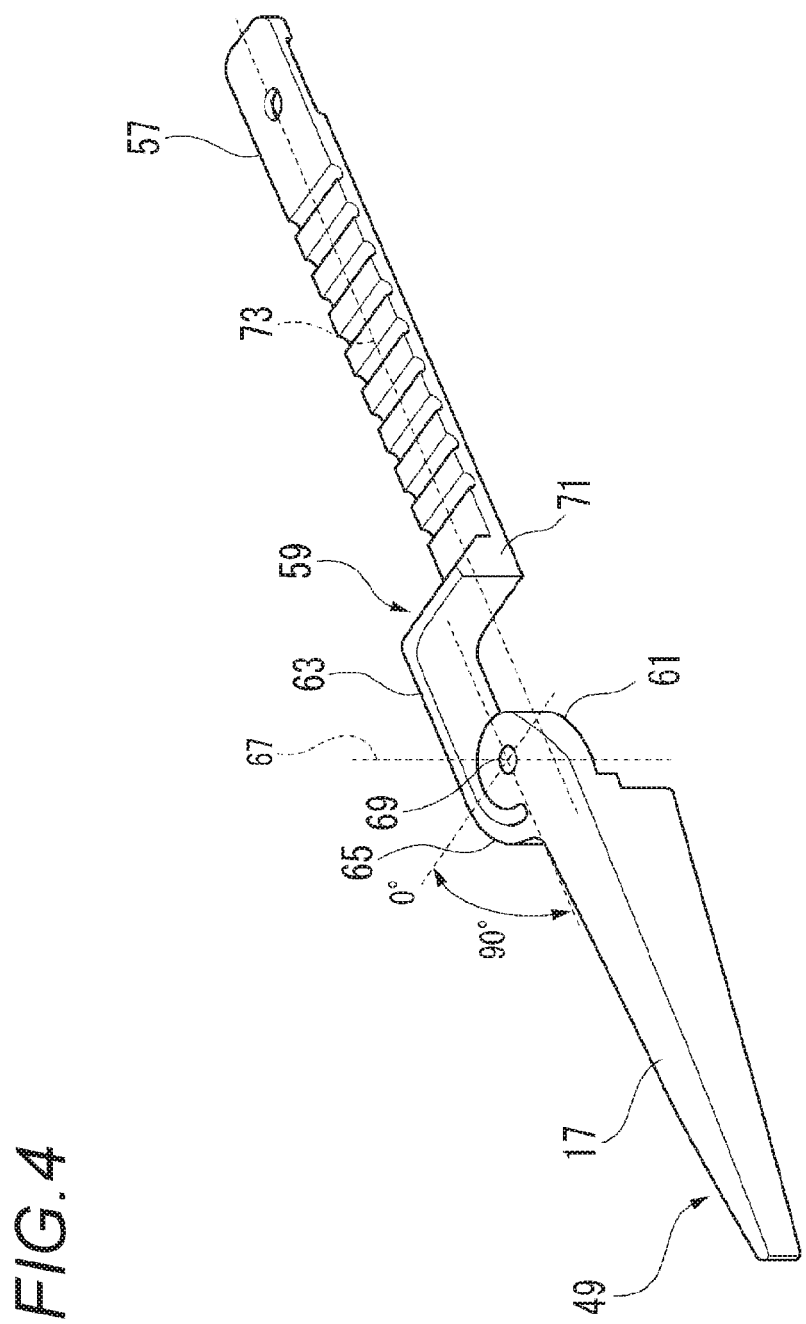
FIG. 4 is a perspective view of the flexible actuating body illustrated in FIG. 3.

FIG. 4 is a perspective view of the flexible actuating body illustrated in FIG. 3.

Based on the pushing and pulling of the plate spring (for example, a horizontal plate spring 57, a first outer horizontal plate spring 53, a second outer horizontal plate spring 55, or a combination thereof which will be described later), the manipulator 11 has a configuration in which the actuators 17 of each of the first flexible actuating body 49 and the second flexible actuating body 51 are operated with multiple degrees of freedom by deforming each of a part of the first flexible actuating body 49 and a part of the second flexible actuating body 51. In the embodiment, since the end effector is described as a capturing device, one pair of first flexible actuating body 49 and the second flexible actuating body 51 is used as a flexible actuating body.

The first flexible actuating body 49 and the second flexible actuating body 51 are used by inverting the same object upside down. Therefore, hereinafter, the first flexible actuating body 49 will be described as a representative example of a flexible actuating body.

As illustrated in FIG. 4, in the first flexible actuating body 49, the horizontal plate spring 57, a curved vertical plate spring 59, a shaft body 61, and the actuator 17 are integrally formed. As a material of the first flexible actuating body 49, for example, Ni—Ti (nickel titanium) which is excellent in biocompatibility, a wide elastic range, and corrosion resistance, is used. The horizontal plate spring 57 is formed in a long rectangular shape along the longitudinal direction of the outer tube 21. The horizontal plate spring 57 has a shape of a plate spring with grooves, and by employing such a shape, unidirectionality of deformation increases, twisting is restrained, and it is possible to operate the manipulator 11 with higher positioning accuracy. In other words, the deformation direction of the first flexible actuating body 49 is controlled by the shape of the horizontal plate spring 57 so that the positioning of the end effector is possible. For example, the horizontal plate spring 57 can be formed with a plate thickness of 0.4 mm, and can be formed with a plate thickness of a groove portion to be 0.2 mm.

The curved vertical plate spring 59 stands upright having a plate surface perpendicular to a plate surface of the horizontal plate spring 57, and the base end of the curved vertical plate spring 59 is connected to one end in the longitudinal direction of the horizontal plate spring 57. The curved vertical plate spring 59 protrudes to one side in a plate width direction of the horizontal plate spring 57 (for example, in a direction toward an upper left side of the paper surface of FIG. 4), and extends along the longitudinal direction of the horizontal plate spring 57. In the curved vertical plate spring 59, the tip end in the extending direction is an R portion 65, as an example of a bent portion in which the tip end in the extending direction bends in a direction opposite to the protruding direction of a bent portion 63. The curved vertical plate spring 59 is provided with the R portion 65 at a connecting part with the shaft body 61, and accordingly, efficient power transmission can be performed during the deformation operation of the first flexible actuating body 49 to make it easy to perform the deformation operation. For example, the curved vertical plate spring 59 can be formed with a thickness of the curved portion 63 to be 0.3 mm.

In the shaft body 61, the tip end of the R portion 65 of the curved vertical plate spring 59 is connected to the outer circumference of the shaft body 61. The shaft body 61 is freely rotatable being supported by a rotation center 67 perpendicular to the plate surface of the horizontal plate spring 57. More specifically, a pin hole 69 is bored in the shaft body 61. The pin 47 (refer to FIG. 2) is inserted into the pin hole 69 coaxially to the rotation center 67. Both ends of the pin 47 are supported by the holder 45. The holder 45 is supported by one pair of outer horizontal plate springs (that is, the first outer horizontal plate spring 53 and the second outer horizontal plate spring 55).

In the shaft body 61, a case where a radial position on the side on which the curved portion 63 protrudes from the rotation center 67 is 0°, the R portion 65 is connected to the outer circumference at a position of approximately 90° counterclockwise in FIG. 4. The R portion 65 is connected to the shaft body 61 at a position of 90° from a position of 0° of the outer circumference. It is preferable that the R portion 65 is connected to the shaft body 61, for example, in the range from the position of 0° to 120° of the outer circumference, from the viewpoint of space efficiency.

The actuator 17 is provided to protrude to the outside of rotation radius (that is, in the radial direction) at the outer circumference of the shaft body 61. In the embodiment, the actuator 17 is connected to the outer circumference of the shaft body 61 of which the base end substantially matches the connection position of the R portion 65. The actuator 17 which configures the capturing device has a plate width along the rotation center 67 and is formed in a substantially pyramid shape in which the plate width and the plate thickness gradually decrease toward the protrusion tip end.

In addition, as illustrated in FIG. 3, in the manipulator 11, the first flexible actuating body 49 on one side and the second flexible actuating body 51 on the other side are overlapped such that the protruding direction of the curved portion 63 of the first flexible actuating body is opposite to the protruding direction of the curved portion 63 of the second flexible actuating body. The first flexible actuating body 49 and the second flexible actuating body 51 are assembled such that one pair of shaft bodies 61 overlaps each other in the direction along the rotation center 67 and one pair of shaft bodies 61 and the actuator 17 have the same height in the direction along the rotation center 67.

The first flexible actuating body 49 and the second flexible actuating body 51 are linked to each other to be freely rotatable about the same rotation center 67 by the pin 47 that penetrates the shaft bodies 61 of both of the first flexible actuating body 49 and the second flexible actuating body 51. The first flexible actuating body 49 and the second flexible actuating body 51 which are integrally assembled are accommodated in the outer tube from the other end in the longitudinal direction to the middle part in the longitudinal direction of the horizontal plate spring 57 of each of the first flexible actuating body 49 and the second flexible actuating body 51.

The first flexible actuating body 49 and the second flexible actuating body 51 are disposed such that each of the actuators 17 in a state where each of the shaft bodies 61 overlaps each other. Therefore, the actuator 17 of the first flexible actuating body 49 illustrated in FIG. 3 becomes the actuator 17 on the lower right side of the paper surface of FIG. 2. In addition, the actuator 17 of the second flexible actuating body 51 illustrated in FIG. 3 becomes the actuator 17 on the upper left side of the paper surface of FIG. 2. Therefore, one pair of actuators 17 is rotated in a direction of approaching each other (that is, gripping) by pulling the first flexible actuating body 49 and the second flexible actuating body 51 at the same time. Accordingly, when performing a gripping operation, buckling which occurs in the horizontal plate spring 57 and the curved vertical plate spring 59 can be avoided, and a large gripping force can be obtained.

In the first flexible actuating body 49, a right-angled triangular reinforcing portion 71 is fixed to the corner at which the horizontal plate spring 57 and the curved vertical plate spring 59 are connected to each other. The reinforcing portion 71 has one pair of orthogonal side portions. One side of the reinforcing portion 71 is fixed to the horizontal plate spring 57. In addition, the other side portion of the reinforcing portion 71 is fixed to the curved vertical plate spring 59. Accordingly, when the force from the horizontal plate spring 57 is applied to the curved vertical plate spring 59, the curved vertical plate spring 59 becomes unlikely to twist.

In addition, in the first flexible actuating body 49, the rotation center 67 of the shaft body 61 is disposed on an extension line of the axis line 73 which passes through the center in the plate width direction of the horizontal plate spring 57. In other words, the first flexible actuating body 49 has a shape in which only the curved vertical plate spring 59 bulges from one side from the horizontal plate spring 57, the shaft body 61, and the actuator 17 which are disposed substantially linearly.

Figure 5:
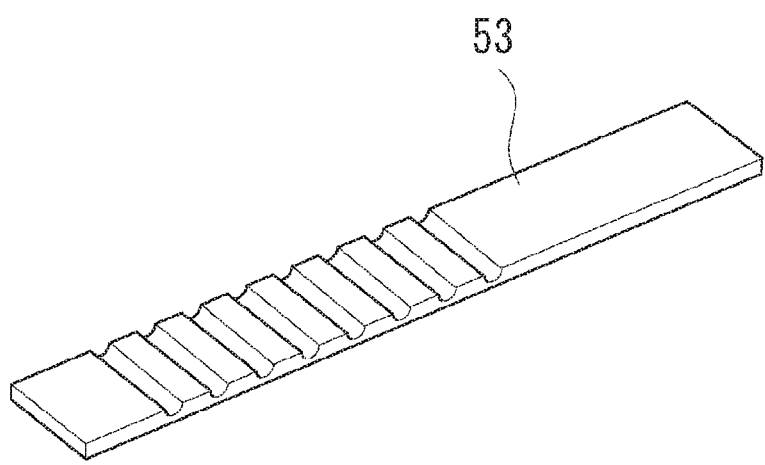
FIG. 5 is a perspective view of the outer horizontal plate spring illustrated in FIG. 3.

FIG. 5 is a perspective view of the outer horizontal plate spring illustrated in FIG. 3.

The manipulator 11 can include one pair of first outer horizontal plate spring 53 and the second outer horizontal plate spring 55. The first outer horizontal plate spring 53 and the second outer horizontal plate spring 55 can be used by inverting the same object upside down. Hereinafter, the first outer horizontal plate spring 53 will be described as a representative example of the outer horizontal plate spring. In the first outer horizontal plate spring 53 illustrated in FIG. 5, the object illustrated in FIG. 3 is inverted upside down.

For the first outer horizontal plate spring 53, similar to the first flexible actuating body 49, for example, Ni—Ti (nickel titanium) which is excellent in biocompatibility, a wide elastic range, and corrosion resistance, is used. The first outer horizontal plate spring 53 is formed in a long rectangular shape along the longitudinal direction of the outer tube 21. Similar to the horizontal plate spring 57, the first outer horizontal plate spring 53 has a plate spring shape with grooves, and by employing such a shape, the unidirectionality of deformation increases, the twist is suppressed, and it is possible to operate the manipulator 11 with higher positioning accuracy. In other words, the deformation direction of the first flexible actuating body 49 can be controlled by the shape of the first outer horizontal plate spring 53, and the positioning of the end effector is possible. For example, the first outer horizontal plate spring 53 can be formed with a plate thickness of 0.4 mm, and can be formed with the plate thickness of a groove portion to be 0.2 mm.

The manipulator 11 includes the holder 45 which supports both ends of the pin 47 penetrating one pair of overlapping shaft bodies 61. One end of one pair of first outer horizontal plate spring 53 and the second outer horizontal plate spring 55 are connected to the holder 45.

As illustrated in FIG. 2, the holder 45 has one pair of parallel holding plates 75 which are separated from each other. One holding plate 75 is formed in a semicylindrical shape with a tip end curved surface formed by cutting a rotating body obtained by rotating an ellipse around a major axis along the major axis. Both of one pair of holding plates 75 which are separated from each other are connected by each of side plates 77. As a result, the holder 45 has an internal space having a shape of a rectangular hole when viewed from the front. Both ends of the pin 47 are fixed to one pair of holding plates 75. The holder 45 accommodates a part of the shaft body 61, the curved vertical plate spring 59, the first outer horizontal plate spring 53, and the second outer horizontal plate spring 55, in the internal space.

In addition, one pair of parallel guides 79 is formed on the holder 45 so as to protrude from each of the side plates 77 toward the outer tube 21. One pair of guides 79 are in contact with each curved outer surface 81 (refer to FIG. 3) of the curved vertical plate spring 59 in one pair of first flexible actuating body 49 and the second flexible actuating body 51. As the guide 79 is in contact with the curved outer surface 81 of the curved vertical plate spring 59 from the outside, the deformation operation which bulges out of the curved vertical plate spring 59, and thus, it is possible to effectively transmit the power to the R portion 65, and the deformation operation is easily performed.

In addition, in the manipulator 11, one pair of spacers 83 which sandwiches the horizontal plate springs 57 of each of the first flexible actuating body 49 and the second flexible actuating body 51 from both sides in the plate width direction is fixed to the inner surface of the outer tube 21. One pair of spacers 83 is respectively in contact with one pair of side end surfaces along the longitudinal direction of one pair of horizontal plate springs 57. Accordingly, one pair of spacers 83 restricts the movement of the horizontal plate spring 57 in the plate width direction in the outer tube.

Next, a controller 85 that controls the slide driving device 19 and the rotation driving device 15 of the manipulator 11 will be described.

The operation of the manipulator 11 is controlled by the controller 85 illustrated in FIG. 1. The controller 85 includes a control computer 87 and a motor driver 89. The controller 85 controls the operation of the slide driving device 19 and the rotation driving device 15. The slide driving device 19 includes a ball screw 91 and a DC motor 93. The slide driving device 19 controls each of the positions of the four sliders of the first outer sliders 29, the first slider 31, the second slider 33, and the second outer slider 35 in the longitudinal direction of the outer tube 21 illustrated in FIG. 1. The slide driving device 19 operates based on an instruction from the controller 85.

The rotation driving device 15 includes a gear unit 95 and a DC motor 97. The rotation driving device 15 controls the rotation direction and the rotation angle of the end cap 23 at the rear end in the longitudinal direction of the outer tube 21 illustrated in FIG. 1. The rotation driving device 15 operates based on an instruction from the control unit 85.

Next, the operation of the manipulator 11 will be described.

In the manipulator 11, the actuator 17 operates with multiple degrees of freedom with respect to the outer tube 21. In other words, one pair of actuators 17 can move in a direction (an arrow a direction in FIG. 2) in which one pair of actuators 17 move close to and away from each other. The manipulator 11 can rotate in the forward and reverse directions (an arrow b direction in FIG. 2) around the rotation center 67 of the shaft body 61 while one pair of actuators 17 is closed. The holder 45 can be displaced in the bending direction of the outer horizontal plate spring (an arrow c direction in FIG. 2). It is possible to move the holder 45 back and forth in the direction along the center axis of the outer tube 21 (an arrow d direction in FIG. 2). The manipulator 11 can further rotate the holder 45 and the outer tube 21 integrally (an arrow e direction in FIG. 2) via the end cap 23 by the rotation driving device 15.

Figure 6:
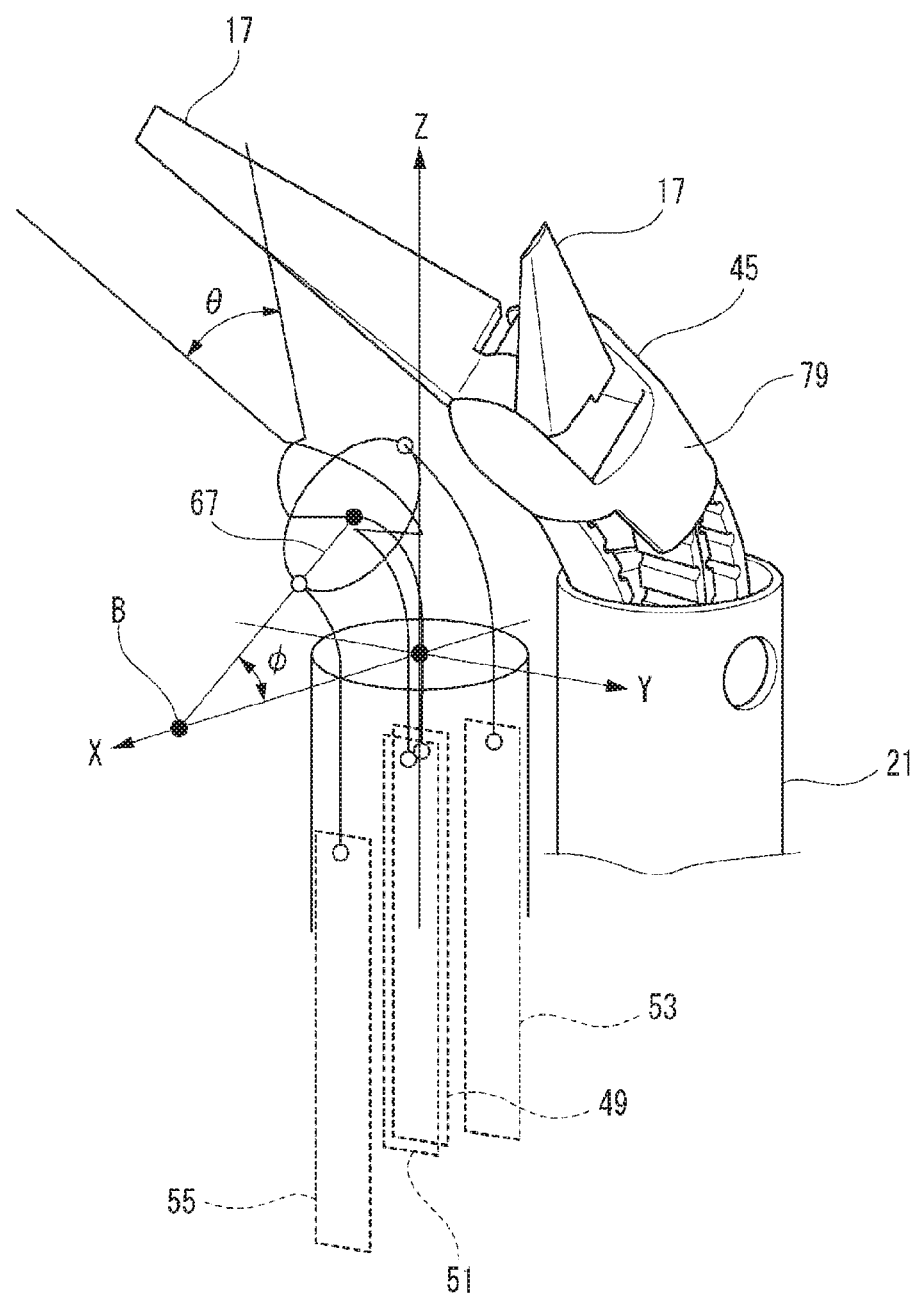
FIG. 6 describes a displacement direction of an actuator.

FIG. 6 describes the displacement direction of the actuator 17.

Here, in order to make it easy to describe the operation at the tip end part of the manipulator 11, the direction of operation is defined. The tip end surface of the outer tube 21 is a plane orthogonal to the center axis of the outer tube 21 and has a circular shape centered on the center axis. At this time, the center axis of the outer tube 21 is "Z-axis". In the manipulator 11 in a state where the holder 45 is not displaced (a state illustrated in FIG. 2), the axis which passes through the Z-axis on the surface including the tip end surface of the outer tube 21 and has the same direction as that of the rotation center 67 of the pin 47 is defined as "X-axis". The axis which passes through the Z-axis on the surface including the tip end surface of the outer tube 21 and is orthogonal to the X-axis, is defined as "Y-axis". A narrow angle of one pair of actuators 17 opened by rotating about the rotation center 67 is set to "θ". When the plate spring is deflected in the X-axis direction and the holder 45 is displaced (tilted), an angle formed by the rotation center 67 of the pin 47 and the X-axis is set to "k". At this time, a point at which the rotation center 67 of the pin 47 intersects with the X-axis is a bending center B.

The manipulator 11 tilts the end effector with the distance from the tip end surface of the outer tube 21 to the pin 47 as a bendable range. A distance P (refer to FIG. 2) from the tip end surface of the outer tube 21 to the rotation center 67 of the pin 47 is set to be, for example, 7.5 mm. The distance P is shorter than the equivalent distance of 9 mm in the above-described "da Vinci surgical system". Accordingly, it is possible to reduce the bending radius when the end effector tilts. This contributes to the ease of a smooth approach to a narrow part (for example, an affected area), for example, in laparoscopic surgery.

Figure 9:
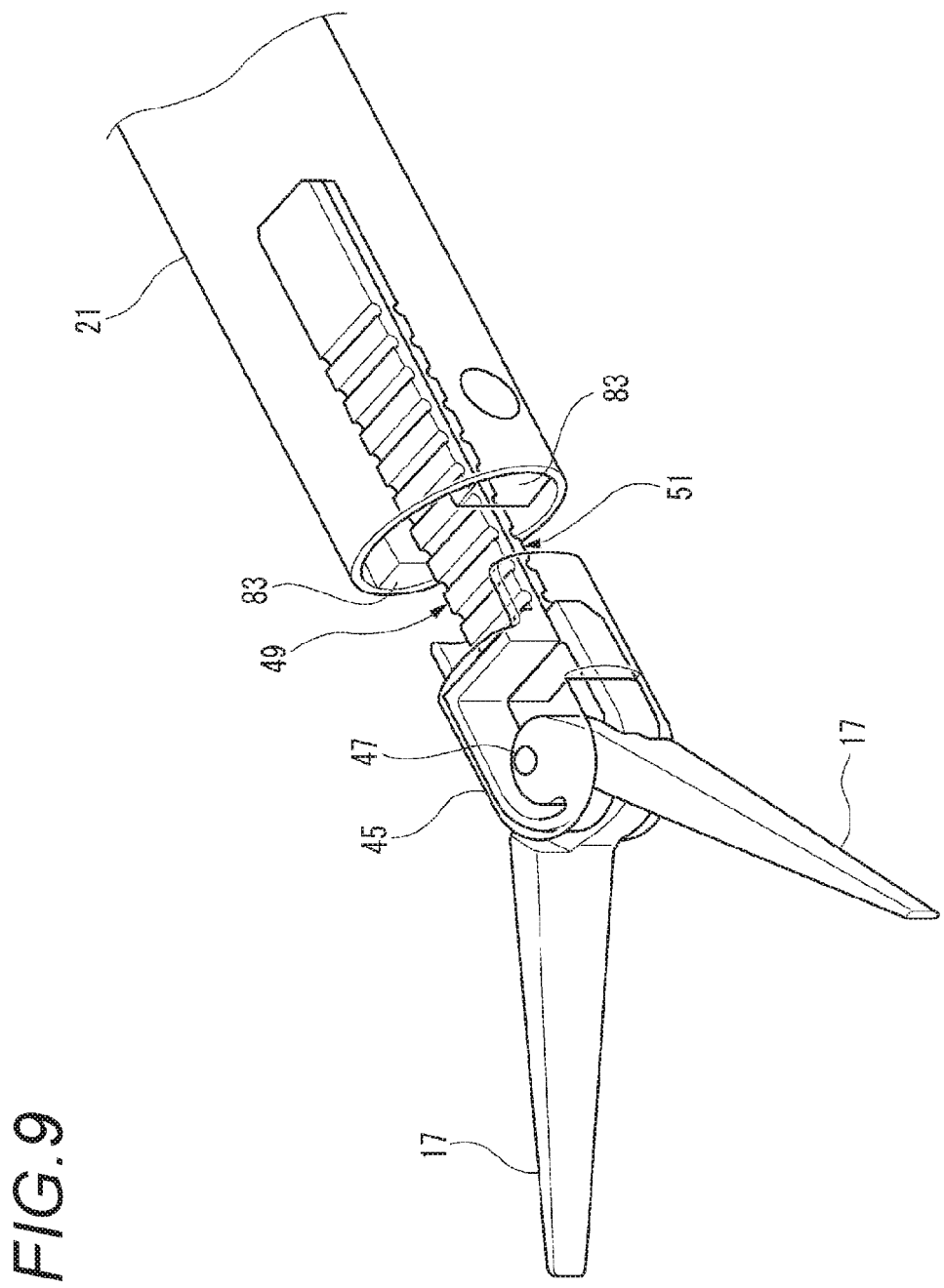
FIG. 9 is an enlarged perspective view of a main part of the manipulator in which the actuator is open.
Figure 10:
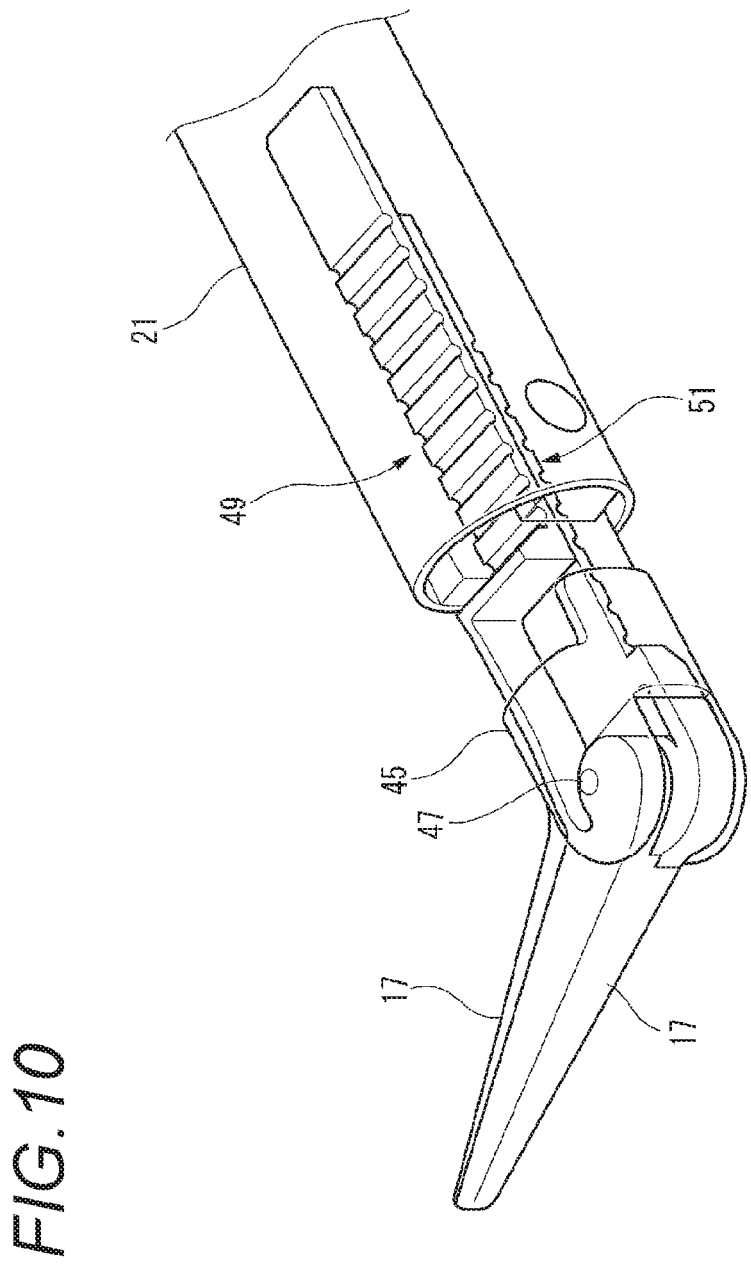
FIG. 10 is an enlarged perspective view of the main part of the manipulator in which the actuator rotates in a −Y direction.

FIG. 7 describes an operation illustrating the displacement direction of the actuator 17 by one pair of horizontal plate springs 57. FIG. 8 describes an operation illustrating the displacement direction of the actuator 17 by one pair of outer horizontal plate springs. FIG. 9 is an enlarged perspective view of a main part of the manipulator 11 in which the actuator 17 is open. FIG. 10 is an enlarged perspective view of the main part of the manipulator 11 in which the actuator 17 has rotated in the −Y direction.

In the manipulator 11, as illustrated in FIG. 7, when the horizontal plate spring 57 of the first flexible actuating body 49 and the horizontal plate spring 57 of the second flexible actuating body 51 are pushed at the same time (that is, pushed to the actuator 17 side), one pair of shaft bodies 61 rotates in the reverse direction. In other words, as illustrated in FIG. 9, one pair of actuators 17 are open. In addition, in the manipulator 11, when the horizontal plate spring 57 of the first flexible actuating body 49 and the horizontal plate spring 57 of the second flexible actuating body 51 are pulled at the same time (that is, pulled to the side opposite to the actuator 17 side), one pair of shaft bodies 61 rotates in the direction reverse to that when one pair of shaft bodies 61 is opened. In other words, as illustrated in FIG. 2, one pair of actuators 17 are closed.

In the manipulator 11, when the horizontal plate spring 57 of the first flexible actuating body 49 is pulled and the horizontal plate spring 57 of the second flexible actuating body 51 is pushed, as illustrated in FIG. 10, one pair of actuators 17 rotates clockwise in FIG. 2 about the rotation center 67 while being closed, and tilts to the −Y-axis side. In addition, in the manipulator 11, when the horizontal plate spring 57 of the first flexible actuating body 49 is pushed and the horizontal plate spring 57 of the second flexible actuating body 51 is pulled, one pair of actuators 17 rotates counterclockwise in FIG. 2 about the rotation center 67 while being closed, and tilts to the Y-axis side.

In the manipulator 11, as illustrated in FIG. 8, when the first outer horizontal plate spring 53 and the second outer horizontal plate spring 55 are pushed at the same time, one pair of actuators 17 advances in the Z direction. In addition, in the manipulator 11, when the first outer horizontal plate spring 53 and the second outer horizontal plate spring 55 are pulled at the same time, one pair of actuators 17 retreats in the −Z direction. In addition, during the forward and backward movements of the first outer horizontal plate spring 53 and the second outer horizontal plate spring 55, the first flexible actuating body 49 and the second flexible actuating body 51 are driven or pushed and pulled at the same time.

Figure 11:
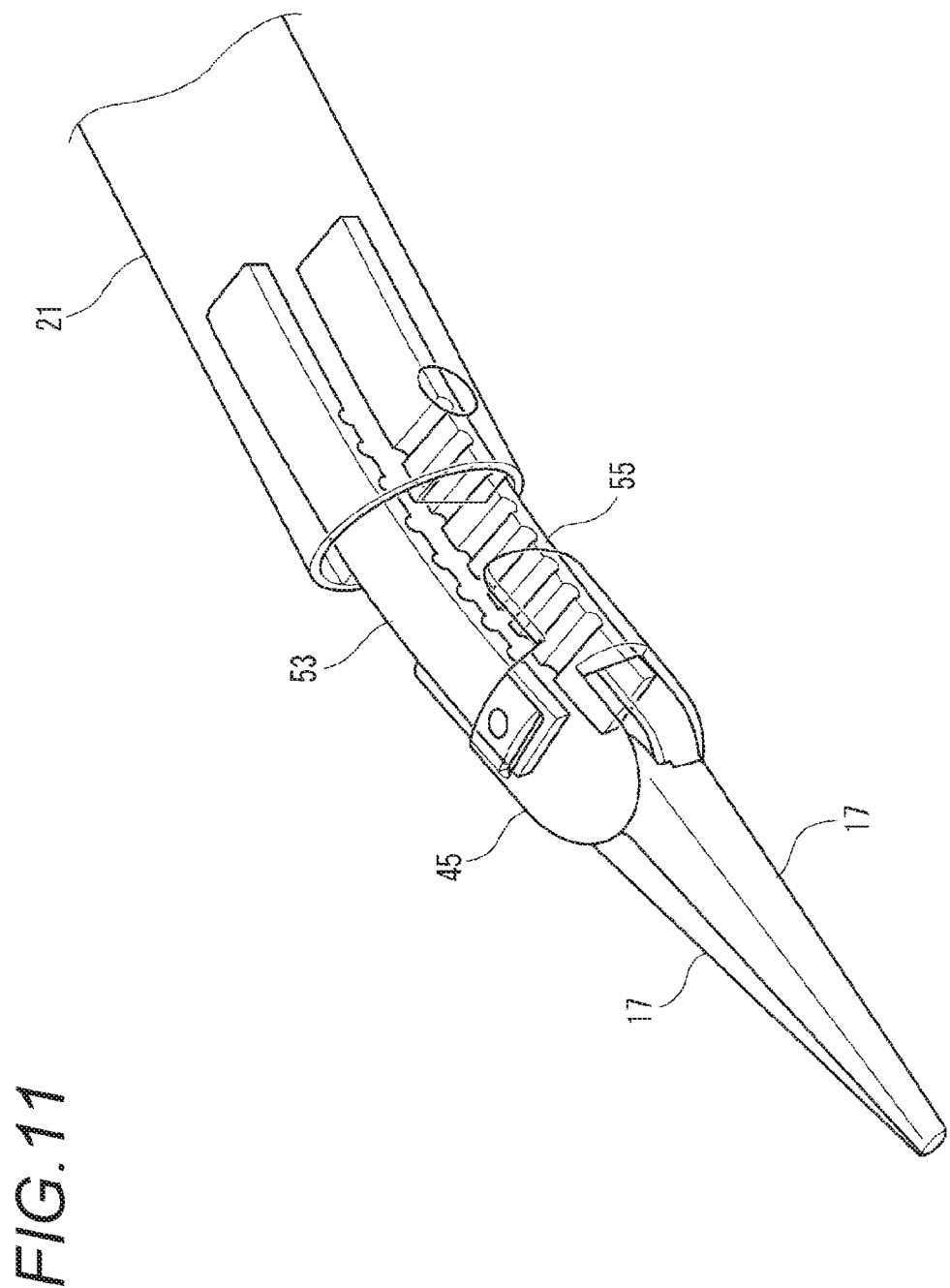
FIG. 11 is an enlarged perspective view of the main part of the manipulator in which the actuator is displaced in an X direction.

FIG. 11 is an enlarged perspective view of the main part of the manipulator 11 in which the actuator 17 has been displaced in the X direction.

In the manipulator 11, when the first outer horizontal plate spring 53 is pushed and the second outer horizontal plate spring 55 is pulled, as illustrated in FIG. 11, one pair of actuators 17 tilts to the X-axis side. In addition, in the manipulator 11, when the first outer horizontal plate spring 53 is pulled and the second outer horizontal plate spring 55 is pushed, one pair of actuators 17 tilts to the −X-axis side.

Figure 12:
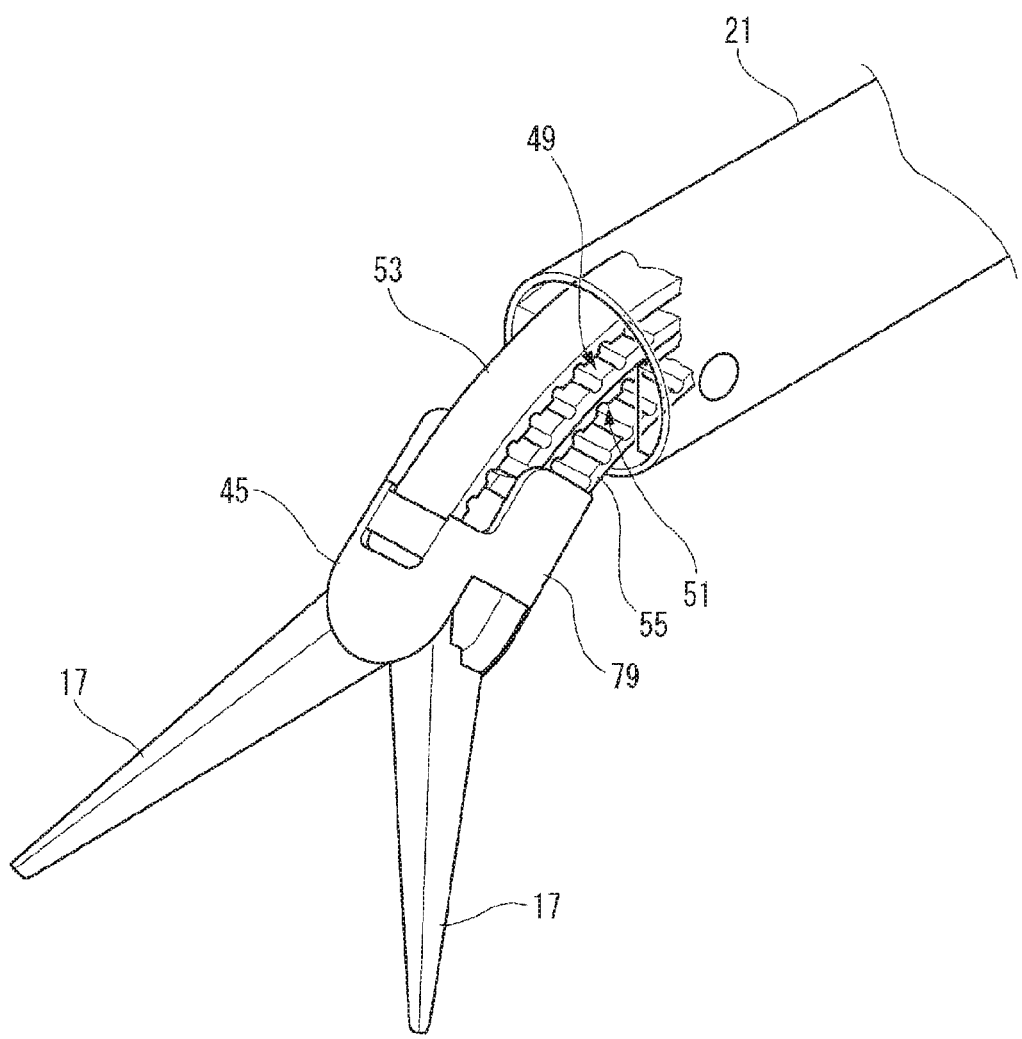
FIG. 12 is an enlarged perspective view of the main part of the manipulator in which the actuator is open and displaced in the X direction.

FIG. 12 is an enlarged perspective view of the main part of the manipulator 11 in which the actuator 17 has been open and displaced in the X direction.

The manipulator 11 can move the bending center B (refer to FIG. 6) by changing pushing and pulling amounts of the first outer horizontal plate spring 53 and the second outer horizontal plate spring 55. In addition, as illustrated in FIG. 12, the manipulator 11 can open and close one pair of actuators 17 by changing the pushing and pulling amounts of the first flexible actuating body 49 and the second flexible actuating body 51 at the same time as the movement of the bending center B.

The manipulator 11 obtains the target values of feeding amounts of the first outer slider 29, the first slider 31, the second slider 33, and the second outer slider 35 of the manipulator 11 with respect to a target bending angle by the control computer 87, transmits a control signal from the motor driver 89, drives the ball screw 91 with the DC motor 93 in the slide driving device 19, and accordingly, the tip end of the manipulator 11 (that is, the end effector, and more specifically, one pair of actuators 17) is operated. Accordingly, as illustrated in FIG. 12, the manipulator 11 can open and close one pair of actuators 17 while bending the end effector to the target bending angle $\phi$. Furthermore, the manipulator 11 changes the pushing and pulling amounts of the first flexible actuating body 49 and the second flexible actuating body 51 while changing the pushing and pulling amounts of the first outer horizontal plate spring 53 and the second outer horizontal plate spring 55, and accordingly, the tip end of the end effector can be swiveled in any direction of 360° around the Z-axis.

Next, the operation of the configuration of the above-described manipulator 11 and the effect of the operation will be specifically described.

In the manipulator 11 of the embodiment, the horizontal plate spring 57, the curved vertical plate spring 59, and the shaft body 61 are disposed in series on the same plane, and a flexible actuating body (that is, the first flexible actuating body 49 and the second flexible actuating body 51) is configured. The curved vertical plate spring 59 is connected to the horizontal plate spring 57 in a direction in which the plate surface stands upright. In other words, the horizontal plate spring 57 and the curved vertical plate spring 59 are connected to each other of which the plate surfaces are orthogonal to each other. The shaft body 61 is supported to be freely rotatable at the rotation center 67 perpendicular to the plate surface of the horizontal plate spring 57.

When the other end in the longitudinal direction of the horizontal plate spring 57 is pressed in the direction along the longitudinal direction, in a case where the shaft body 61 is supported so as to be immovable within the same plane as described above, the flexible actuating body (that is, the first flexible actuating body 49 and the second flexible actuating body 51) is deformed in a direction in which the curved vertical plate spring 59 is further curved. The deformation occurs within the elastic limit of the curved vertical plate spring 59. Therefore, elongation and shrinkage (permanent distortion) do not occur in the flexible actuating body. Since the plate surfaces of the horizontal plate spring 57 and the curved vertical plate spring 59 are orthogonal to each other, the deformation direction of the curved vertical plate spring 59 changes by 90°. Accordingly, the curved vertical plate spring 59 can deform along the above-described same plane. In the curved vertical plate spring 59, most of the internal stress accumulated by the deformation is an elastic restoring force. A part of this elastic restoring force acts as a component force in a tangential direction of the outer circumference of the shaft body which generates a moment with respect to the shaft body 61. In the manipulator 11 provided with one pair of guides 79 in the holder 45, deformation of the curved vertical plate spring 59 mainly occurs in the R portion 65.

In addition, when the other end in the longitudinal direction of the horizontal plate spring 57 is pulled in a direction along the longitudinal direction, the flexible actuating body (that is, the first flexible actuating body 49 and the second flexible actuating body 51) is deformed in a direction of eliminating the curve (linearly approaching direction) of the curved vertical plate spring 59. In the curved vertical plate spring 59, a part of the elastic restoring force accumulated by the deformation acts as a component force in the tangential direction of the outer circumference of the shaft body which generates a moment in a direction reverse to the above-described direction, with respect to the shaft body 61. As a result, the shaft body 61 can rotate the actuator 17 provided in the shaft body 61 in the reverse direction about the rotation center 67 by pushing and pulling the horizontal plate spring 57.

Furthermore, the flexible actuating body (that is, the first flexible actuating body 49 and the second flexible actuating body 51) allows deformation in the direction in which the horizontal plate spring 57 is displaced to the front and rear plate surface sides (the X-axis side and the −X-axis side in FIG. 6). Accordingly, the flexible actuating body does not prevent the actuator 17 from tilting in the same direction.

In this manner, the manipulator 11 which uses the flexible actuating body can eliminate the wire which is common means of the related art, and operate the actuator 17 with multiple degrees of freedom.

The flexible actuating body (that is, the first flexible actuating body 49 and the second flexible actuating body 51) has no concern of stretching or breaking unlike a wire. Accordingly, it is possible to improve the durability, and to extremely reduce the number of replacements of the manipulator 11. Since the flexible actuating body (that is, the first flexible actuating body 49 and the second flexible actuating body 51) does not extend similar to a wire, the rotation accuracy or the positional accuracy of the actuator 17 can be enhanced. Furthermore, since the flexible actuating body (that is, the first flexible actuating body 49 and the second flexible actuating body 51) is a single member, a simple machine configuration can be realized, sterilization or cleaning are extremely easy. Moreover since the flexible actuating body (that is, the first flexible actuating body 49 and the second flexible actuating body 51) does not need to be wound around a gear or a pulley unlike a wire, it is possible to make the attachment and detachment simple and easy between the manipulator 11 and driving means.

In addition, the flexible actuating body (that is, the first flexible actuating body 49 and the second flexible actuating body 51) does not need to use a plurality of links and passive joints unlike a link mechanism. Accordingly, it becomes easy to reduce the number of components, the size, and weight. According to this, it becomes easy to reduce the manufacturing costs. In addition, reduction in weight reduces the moving mass of the end effector, which makes it possible to reduce the inertial force. Accordingly the positioning control of the end effector becomes easy and the positioning accuracy can be enhanced. In addition, since a wire, a pulley, a plurality of links, or a passive joint is not used, the bending radius when displacing the actuator 17 together with the shaft body 61 can be reduced.

In the manipulator 11, the connecting portion between the horizontal plate spring 57 and the curved vertical plate spring 59 is reinforced by the reinforcing portion 71, and rigidity is enhanced. Accordingly, due to the force transmitted from the horizontal plate spring 57, the curved vertical plate spring 59 is unlikely to twist. As a result, the transmission efficiency of the force transmitted from the horizontal plate spring 57 to the curved vertical plate spring 59 can be enhanced.

Since the protruding directions of the curved vertical plate springs 59 of one pair of flexible actuating bodies are reverse to each other, the manipulator 11 pushes or pulls the other ends in the longitudinal direction of each of the horizontal plate springs 57 at the same time, and accordingly, each of the capturing portions 17 can be moved close to and away from each other. In other words, when the actuator 17 is a capturing device, pinching becomes possible. When the actuator 17 is scissors, cutting is possible. In the manipulator 11, by pushing or pulling the other ends in the longitudinal direction of one pair of horizontal plate springs 57 at the same time in the opposite directions, one pair of actuators 17 can be rotated about the rotation center 67 of the shaft body 61 in the same direction. In other words, when the actuator 17 is a capturing device, it is possible to rotate in forward and reverse directions while the capturing device is closed.

In addition, in the manipulator 11, one pair of curved vertical plate springs 59 protrudes in the reverse direction. Meanwhile, the horizontal plate springs 57 of the pair of flexible actuating bodies overlap each other without deviation in the longitudinal direction and in the plate width direction. In the manipulator 11, the rotation center 67 of each of the shaft bodies 61 is commonly arranged and fixed by one single pin 47 on the extension line of the axis line 73 of the horizontal plate spring 57. Accordingly, the manipulator 11 can ensure a curved shape while suppressing the protrusion width between the projecting ends in the bending direction of one pair of curved vertical plate springs 59 to be small.

In addition, in the manipulator 11, one pair of flexible actuating bodies overlaps such that one pair of horizontal plate springs 57 sandwiches the center axis of the outer tube 21. In the manipulator 11, furthermore, one pair of outer horizontal plate springs (the first outer horizontal plate spring 53 and the second outer horizontal plate spring 55) is disposed on the outside of one pair of horizontal plate springs 57 sandwiching the horizontal plate springs 57. In other words, in the outer tube 21, one pair of horizontal plate springs 57 and one pair of outer horizontal plate springs are arranged in four layers. Each of the plate springs is pushed and pulled independently. One end in the longitudinal direction of one pair of outer horizontal plate springs is fixed to the holder 45. The tip end surface of the outer tube 21 and the holder 45 are disposed to be separated from each other. Therefore, between the tip end surface of the outer tube 21 and the holder 45, one pair of horizontal plate springs 57 and one pair of outer horizontal plate springs sandwiching the horizontal plate springs which overlaps in four layers are exposed.

In the manipulator 11, when one pair of outer horizontal plate springs are pushed and pulled in reverse direction, one pair of outer horizontal plate springs is deformed (bent) in a direction of being inclined to one outer horizontal plate spring side together, and one pair of outer horizontal plate springs is deformed (bent) in a direction of being inclined to the other outer horizontal plate spring together. The holder 45 is displaced (that is, tilted) by the bending of one pair of outer horizontal plate springs. At this time, one pair of horizontal plate springs 57 disposed between one pair of outer horizontal plate springs also allows the bending in the same direction.

In this manner, the manipulator 11 pushes and pulls the other ends in the longitudinal direction of the horizontal plate springs 57 in one pair of flexible actuating bodies to move in the direction a (refer to FIG. 2) of moving close to or being separated from (opens and closes) one pair of actuators 17 (one degree of freedom).

By pushing and pulling the other end in the longitudinal direction of the horizontal plate spring 57 in one pair of flexible actuating bodies in the reverse direction, one pair of actuators 17 can rotate in the forward and reverse directions b (refer to FIG. 2) about the rotation center 67 of the shaft body 61 (2 degrees of freedom).

By pushing and pulling one pair of outer horizontal plate springs in the reverse direction, the holder 45 (that is, the actuator 17) can be displaced in the direction c (refer to FIG. 2) of bending of the outer horizontal plate spring (3 degrees of freedom).

In addition, by pushing and pulling all the springs including one pair of flexible actuating bodies and one pair of outer horizontal plate springs in the same direction along the longitudinal direction, one pair of actuators 17 can be moved back and forth in the direction d (refer to FIG. 2) along the center axis of the outer tube 21 (4 degrees of freedom).

In other words, the manipulator 11 can operate the actuator 17 to multiple degrees of freedom (specifically, four degrees of freedom) by applying deformation of the elastic body and performing mechanical power conversion without using a wire or a link mechanism.

In addition, in the manipulator 11, the deformation in the direction in which the curved vertical plate spring 59 is further curved is restricted by the guide 79 that is in contact with the curved outer surface 81. Accordingly, deformation of the curved vertical plate spring 59 in the curved direction due to the reaction force from the shaft body 61 is restricted. As a result, it is possible to apply a large moment to the shaft body 61.

Furthermore, in the manipulator 11, the force which pushes and pulls the horizontal plate spring 57 is converted into a moment that rotates the shaft body 61 and transmitted. At this time, the flexible actuating body receives a force that moves the horizontal plate spring 57 in the plate width direction by the reaction force from the shaft body 61. In the flexible actuating body, movement of the horizontal plate spring 57 in the plate width direction is restricted by the spacer 83. As a result, it is possible to increase the transmission efficiency of the force from the horizontal plate spring 57 to the curved vertical plate spring 59, and to apply a large moment to the shaft body 61.

Therefore, according to the manipulator 11 of the embodiment, it is possible to eliminate wires, to reduce the size, weight, and costs with a small number of components, and it is possible to easily approach the affected area.

Above, although the embodiments have been described with reference to the drawings, it is needless to say that the present invention is not limited to such examples. In a case of those skilled in the art, it is apparent that various modification examples or correction examples can be assumed within the scope described in the claims, and it is understood that the modification examples or correction examples belong to the technical scope of the present invention.

Furthermore, in the above-described embodiment, the manipulator may have three or more flexible actuating bodies.

This application is filed based on Japanese Patent Application No. 2015-197194 filed on Oct. 2, 2015, the contents of which are incorporated herein by reference.

INDUSTRIAL APPLICABILITY

The present invention is useful as a manipulator in which wires that serve as a tool for transmitting power to a tip end portion that performs treatment with respect to an affected area can be eliminated, which can reduce the size, weight, and costs with a small number of components, and further which causes easy approach to the affected area.

REFERENCE SIGNS LIST

11: Manipulator
17: Actuator
21: Outer tube
45: Holder
47: Pin
49: First flexible actuating body (flexible actuating body)
51: Second flexible actuating body (flexible actuating body)
53: First outer horizontal plate spring (outer horizontal plate spring)
55: Second outer horizontal plate spring (outer horizontal plate spring)
57: Horizontal plate spring
59: Curved vertical plate spring
61: Shaft body
65: R portion
67: Rotation center
71: Reinforcing portion
73: Axis line
79: Guide
81: Curved outer surface
83: Spacer

The invention claimed is:

1. A manipulator comprising:
at least one flexible actuating body including:
a rectangular horizontal plate spring;
a curved vertical plate spring which stands upright having a plate surface perpendicular to a plate surface of the horizontal plate spring, of which a base end is connected to one end of the horizontal plate spring in a longitudinal direction, which protrudes to one side in a plate width direction of the horizontal plate spring, which extends along the longitudinal direction of the horizontal plate spring, and of which a tip end in the extending direction is a bent portion bent in a direction opposite to the protruding direction;
a shaft body which is connected to a tip end of the bent portion, is supported at a rotation center perpendicular to the plate surface of the horizontal plate spring, and becomes freely rotatable; and
an end effector which is provided to protrude in a radius direction from an outer circumference of the shaft body.

2. The manipulator according to claim 1, wherein one side portion of a reinforcing portion having one pair of orthogonal side portions is fixed to the horizontal plate spring at a corner at which the horizontal plate spring and the curved vertical plate spring are connected to each other, and the other side portion of the reinforcing portion is fixed to the curved vertical plate spring at the corner.

3. The manipulator according to claim 1,
wherein the at least one flexible actuating body comprises one pair of the flexible actuating bodies,
wherein the pair of the flexible actuating bodies overlaps such that the protruding direction of a curve of the curved vertical plate spring of the one flexible actuating body becomes opposite to the protruding direction of a curve of the curved vertical plate spring of the other flexible actuating body, is linked to each other to be freely rotatable at the rotation center by a common pin penetrating the shaft body of each of the pair of the flexible actuating bodies, and
one pair of the horizontal plate springs in the pair of the flexible actuating bodies is accommodated on the inside of an outer tube from the other ends in the longitudinal direction to middle parts in the longitudinal direction.

4. The manipulator according to claim 3, wherein the rotation center of the shaft body is disposed on an axis line that passes through a center in the plate width direction of the horizontal plate spring.

5. The manipulator according to claim 3, further comprising:
a holder which supports both ends of the pin,
wherein one ends of one pair of outer horizontal plate springs, which sandwiches the horizontal plate springs of the pair of the flexible actuating bodies in parallel, and extends in the same direction as that of the horizontal plate spring, are connected to the holder, and
the pair of outer horizontal plate springs is accommodated inside the outer tube from the other ends in the longitudinal direction to the middle parts in the longitudinal direction.

6. The manipulator according to claim 5, wherein one pair of guides which is in contact with curved outer surfaces of the curved vertical plate springs of each of the pair of the flexible actuating bodies is provided in the holder.

7. The manipulator according to claim 5, wherein one pair of spacers which is in contact with each of one pair of side end surfaces is provided on an inner surface of the outer tube along the longitudinal direction of the horizontal plate spring of each of the pair of the flexible actuating bodies.

8. The manipulator according to claim 1, wherein the end effector is a clamp, a capturing device, a scissors, a stapler, or a needle holder.

* * * * *